United States Patent [19]

Crivello

[11] 3,981,897

[45] Sept. 21, 1976

[54] METHOD FOR MAKING CERTAIN HALONIUM SALT PHOTOINITIATORS

[75] Inventor: James V. Crivello, Elnora, N.Y.

[73] Assignee: General Electric Company, Schenectady, N.Y.

[22] Filed: May 2, 1975

[21] Appl. No.: 574,007

[52] U.S. Cl. .............................. 260/440; 260/446; 260/606.5 P
[51] Int. Cl.² .............................................. C07F 9/66
[58] Field of Search ............. 260/440, 446, 606.5 P

[56] References Cited
UNITED STATES PATENTS 3,585,227  6/1971  Dreyfuss ............................. 260/440

OTHER PUBLICATIONS

Olah et al., J.A.C.S. vol. 96, 3560–3573 (1974).
Chemical Abstracts, vol. 57, 15147 (1962).

*Primary Examiner*—Helen M. S. Sneed
*Attorney, Agent, or Firm*—William A. Teoli; Joseph T. Cohen; Jerome C. Squillaro

[57] ABSTRACT

A method is provided for making certain diarylhalonium salts containing Group Va metal hexafluorides useful as photoinitiators, such as diphenyliodonium hexafluoroarsonate. An intermediate diarylhalonium bisulfate is prepared. Reaction is thereafter effected between the diarylhalonium bisulfate and the source of a counterion, such as $AsF_6^-$, in the form of the corresponding acid or salt. The halonium salt photoinitiators can be used to make UV curable compositions.

7 Claims, No Drawings

METHOD FOR MAKING CERTAIN HALONIUM SALT PHOTOINITIATORS

The present invention realtes to a method for making certain halonium salts such as diphenyliodonium hexafluoroarsonate, which are useful as photoinitiators.

Prior to the present invention, halonium salts such as

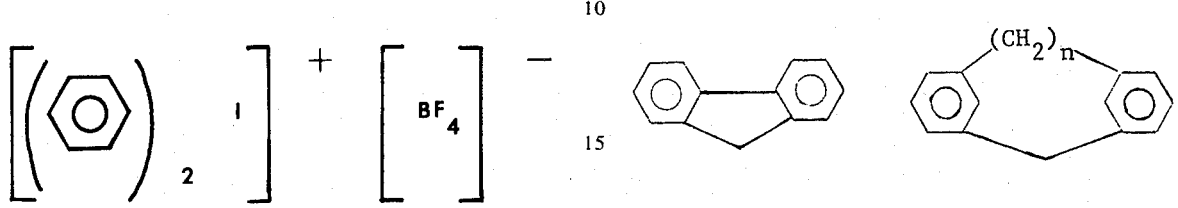

were employed in combination with curable epoxy resins, as shown in my copending application Ser. No. 455,375, filed May 2, 1974, and assigned to the same assignee as the present invention. The halonium salts provide a source of a Lewis-Acid catalyst, which is released during exposure of the epoxy-halonium salt blend to UV radiation resulting in the cure of the epoxy resin.

Halonium salts as shown above, have been prepared using silver compounds, such as silver oxide followed by a strong protonic acid $HYF_6$ or silver tetrafluoroborate, which were reacted with the appropriate diarylhalonium salt, as shown by M. C. Casserio et al., J. Am. Chem. Soc. 81, 336 (1959) or M. C. Beringer et al., J. Am. Chem. Soc. 81, 342 (1959). Although effective results have been achieved from these methods, the high cost of silver compounds rendered these procedures economically unattractive. It would be desirable, therefore, to be able to make halonium salts as described above, capable of serving as photoinitiators for curing epoxy resins without the use of silver compounds.

The present invention is based on the discovery that halonium salts useful as photoinitiators for epoxy resins, can be made by a silver free method based on the direct metathesis of an arylhalonium bisulfate salt of the formula, $$[(R)_a (R^1)_b X]^+ [HSO_4]^- \qquad (1),$$

and hexafluoro compound of the formula, $$MYF_6 \qquad (2)$$

to produce arylhalonium salts of the formula, $$[(R)_a (R^1)_b X]^+ [YF_6]^- \qquad (3),$$

where R is a monovalent aromatic organic radical, $R^1$ is a divalent aromatic organic radical, X is a halogen radical such as I, Br, Cl, etc., M is an element such as hydrogen, Na, K, magnesium, barium, etc., Y is selected from a Group VA element, e.g. P, As and Sb, a is a whole number equal to 0 or 2, b is a whole number equal to 0 or 1, and the sum of a + b is equal to 2, or the valence of X.

Radicals included by R can be the same or different, aromatic carbocyclic or heterocyclic radicals having from 6 to 20 carbon atoms, which can be substituted with from 1 to 5 monovalent radicals selected from $C_{(1-8)}$ alkoxy, $C_{(1-8)}$ alkyl, nitro, chloro, etc., R is more particularly, phenyl, chlorophenyl, nitrophenyl, metoxyphenyl, pyridyl, etc. Radicals included by $R^1$ are divalent radicals such as

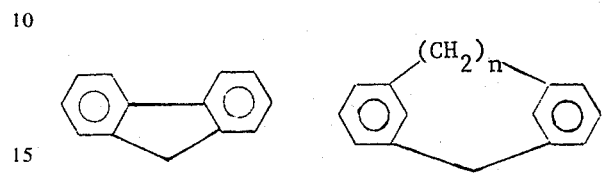

etc.

There is provided by the present invention, a method for making diarylhalonium salts of Formula (3) which comprises, effecting contact under aqueous conditions between an arylhalonium bisulfate salt of Formula (1), and an alkali Group VA metal hexafluoride acid or salt of Formula (2), and thereafter recovering a diarylhalonium Group VA hexafluoride salt from the resulting mixture.

Diarylhalonium bisulfate salts of Formula (1) and methods for making such materials are well known as shown by I. Masson, Nature 139, 150 (1937); I. Masson and E. Raci, J. Chem. Soc., 1718 (1937); L. Masson and W. E. Hanby, J. Chem. Soc., 1699 (1937); D. A. Berry, R. W. Greenlee, W. C. Ellis, and M. M. Baldwin, Twelfth Intl. Congr. Pure and App. Chem., N.Y., N.Y., Sept. 1951, Abstrs. p. 465; and M. C. Casserio, D. T. Glusker and J. D. Roberts, J. Am. Chem. Soc., 81 336 (1959). Some of the diarylhalonium salts of Formula (1) are, for example, diphenyliodonium bisulfate, 4,4'-dichlorodiphenyliodonium bisulfate, 4,4'-dibromodiphenyliodonium bisulfate, 3,3'-dinitrodiphenyliodonium bisulfate, 4,4'-dimethyldiphenyliodonium bisulfate, 4,4'-bissuccinimidodiphenyliodonium bisulfate, 3-nitrodiphenyliodonium bisulfate, 4,4'-dimethoxydiphenyliodonium bisulfate.

Included by the Group VA metal hexafluoride salts of Formula (2) are, for example, $NaPF_6$, $NaAsF_6$, $KSbF_6$, $KAsF_6$, $Ca(PF_6)_2$, $Mg(AsF_6)_2$, $HPF_6$, $HAsF_6$, $HSbF_6$, $Ba(AsF_6)_2$, $Pb(PF_6)_2$, $Zn(AsF_6)_2$, etc.

In the practice of the invention, an aqueous mixture of substantially equal molar amounts of the diarylhalonium bisulfate and the Group VA metal hexafluoride salt is made at a temperature of from 9°C to 100°C. In forming the mixture, the order of addition of the ingredients is not critical.

The halonium salts containing Group VA metal hexafluoride compounds made in accordance with the method of the present invention can be used as photoinitiators for epoxy resins as shown in my copending application Ser. No. 574,006, filed concurrently herewith and assigned to the same assignee as the present invention.

In order that those skilled in the art may be better able to practice the invention, the following examples are given by way of illustrataion and not by way of limitation. All parts are by weight.

EXAMPLE 1

A solution of about 200 parts of sulfuric acid in about 300 parts of acetic was added at a temperature between 0° to 3°C to a mixture, while it was being agitated, of 200 parts of potaassium iodate, about 300 parts of toluene, about 900 parts of acetic acid and about 400 parts of acetic anhydride. The mixture was then stirred for 11 hours after all of the sulfuric acid and the acetic acid had been added. The resulting inorganic salts were removed by filtration and then washed with a small amount of cold glacial acetic acid. A pale yellow solution was obtained which was diluted to twice its volume with water and extracted three times with ether. A small amount (0.3 part) of sodium sulfite was added as a reducing agent.

Based on method of preparation, there was obtained a quantitative yield of 4,4'-dimethyldiphenyliodonium bisulfate. A slightly warm aqueous solution of substantially equal molar amounts of 4,4'-dimethyldiphenyliodonium bisulfate and potassium hexafluoroarsenate was allowed to cool. There was obtained a white crystalline deposit. The products was filtered and washed with distilled water. A second crop of crystals was obtained on further standing. After the crystals were dried overnight, there was obtained 27 parts of a product having a melting point of 148°–152°C. Recrystallization of the product from a water-ethanol mixture resulted in a product having a melting point of 163°–166°C. Based on method of preparation and NMR spectra and elemental alalysis for $C_{14}H_{14}IAsF_6$ calculated: percent C, 33.74; percent H, 2.81; percent As, 15.06; found: percent C, 33.70; percent H, 2.92; percent As, 15.28, the product was 4,4'-dimethyldiphenyliodonium hexafluoroarsenate.

The 3 percent solution of the above halonium hexafluoroarsenate salt in 4-vinylcyclohexenedioxide gave a tack-free film when irradiated for 5 seconds under a General Electric H3T7 medium pressure mercury arc lamp at a distance of 6 inches.

EXAMPLE 2

There was added a solution of 50 parts of sulfuric acid and about 75 parts of acetic acid to a mixture maintained at about 0°C while it was being stirred of 50 parts of potassium iodate, 70 parts of t-butylbenzene and about 225 parts of acetic acid. The resulting mixture was allowed to stand for 3 hours at 0°C and an additional 8 hours at ambient temperature. Salts which were formed in the mixture were removed by filtration, and the resulting solution was diluted to three times its volume with water. The mixture was then extracted three times with ether. There was obtained a pale yellow solution. The solution was divided in two, and there was added to one of the aliquots, 11 parts of potassium hexafluoroarsenate. A white crystalline solid was formed immediately. The mixture was then filtered and the filtrate was dried. There was obtained 14 parts of 4,4'-di-t-butyldiphenyliodonium hexafluoroarsenate having a melting point of 169°–171°C. The identity of the product was based on its method of preparation and its NMR spectrum.

A 3% solution of the above salt in 4-vinylcyclohexenedioxide was coated onto a glass plate. It was then irradiated using a GE H3T7 medium pressure mercury arc lamp at a distance of 6 inches. A tack free, hard film was produced in about 3-5 seconds irradiation.

There was added to the second aliquot of the above-described solution of 4,4'-di-t-butyldiphenyliodonium bisulfate, 9.4 parts of potassium hexafluorophosphate. There was immediately obtained a crytalline solid. It was collected and dried and it weighed 6.5 parts. It had a melting point of 173°–174°C. Based on method of preparation and its NMR spectrum the compound was 4,4'-di-t-butyldiphenyliodonium hexafluorophosphate. A 3% solution of this salt in 4-vinylcyclohexanedioxide cured under the same conditions as described above to a hard tack free film in 20 seconds.

EXAMPLE 3

The above experiment was repeated except that in the metathesis step, there was substituted $KSbF_6$ instead of $KAsF_6$. There was obtained after recrystallization from methylene chloride-diethyl ether, the white crystalline 4,4'-di-t-butyldiphenyliodonium hexafluoroantimonate having a melting point of 163°–165°C. When a 3% solution of this salt in 4-vinylcyclohexene dioxide wasa exposed to the UV light from a GE H3T7 medium pressure mercury arc lamp at a distance of 6 inches, a 3 mil film of the mixture was tack-free within 3 seconds.

EXAMPLE 4

There was added with stirring, 39.36 parts of nitrobenzene to a mixture at 10°C of 7.7 parts of iodine, 20 parts of potassium iodate and 80 parts of sulfuric acid. After stirring for 1 hour at 10°C and then 24 hours at 25°C and finally 40 hours at 45°–50°C, the reaction mixture was cooled to 5°C and diluted with 200 parts cold water. A crude product was separated by vacuum filtration, washed with water and then ether, and then dried. Based on method of preparation, the product was 3,3'-dinitrodiphenyliodonium bisulfate. It was suspended in 250 parts of water, and a solution of 17.1 parts of $KAsF_6$ in 100 parts of water was added. A pale yellow product was formed, which was collected by filtration, washed, and then dried in vacuo. There was obtained 12.1 parts 3,3'-dinitrodiphenyliodonium hexafluoroarsenate having a m.p. of 192°–195°C.

The identity of the compound was confirmed on the basis of its UV and NMR spectra and elemental analysis. Analysis for $C_{12}H_8I_{N2}O_4 AsF_6$ calculated: percent C, 25,9; percent H, 1.43; percent N, 5.0; percent I, 22.6, found: percent C, 26.00; percent H, 1.42; percent N, 5.05; percent I, 22.80.

A mixture prepared by dissolving 3% of the above salt in 4-vinyl-cyclohexene dioxide was subjected to the same conditions of irradiation as described in the previous example. Cure to a tack free state occurred in 3 seconds under these conditions.

EXAMPLE 5

There was slowly added a solution of 150 parts of acetic acid and 180 parts of concentrated sulfuric acid to 198 parts of chlorobenzene, 100 parts of potassium iodate, 450 parts of acetic acid and 216 parts of acetic anhydride at 9°–3°C. The mixture was allowed to stand for 16 hours and then diluted with 500 parts of water. To the resulting solution, there was added 33 parts of $KAsF_6$. On standing a low yield of white crystals was deposited having a m.p. 194°–195°C. The product was identified as 4,4'-dichlorodiphenyliodonium hexafluoroarsenate on the basis of its elemental analysis. Calculated for $C_{12}H_8Cl_2 AsF_6$: percent C, 26.76; percent H, 1.48; percent As, 13.91, found: percent C, 26.85; percent H, 1.59; percent As, 13.72. A 3% solution of the salt in the epoxy monomer, 4-vinylcyclohexene oxide required 5 seconds to cure to a tack-free state under the conditions of irradiation described in the previous example.

Although the above examples are limited to only a few of the very many variables included by the method of the present invention, it should be understood that the present invention broadly includes the use of arylhalonium salts of formula (1) and hexafluoro compounds of formula (2).

What I claim as new and desire to secure by Letters Patent of the United States is:

1. A method for making diarylhalonium salts of the formula,

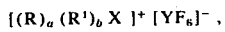

which comprises effecting contact under aqueous conditions between a diarylhalonium bisulfate salt of the formula,

and a Group VA alkali hexafluoro salt of the formula, $MYF_6$ and thereafter recovering the diarylhalonium Group VA hexafluoride compound from the resulting mixture, where R is a monovalent aromatic group, $R^1$ is a divalent aromatic group, X is a halogen radical, M is an element selected from the class of hydrogen, alkali metal and alkaline earth metal, Y is selected from P, As and Sb, is a whole number equal to 0 or 2, b is a whole number equal to 0 or 1, and the sum of a+b is equal to 2, or the valence of X.

2. A method in accordance with claim 1, where X is iodine.
3. A method in accordance with claim 1, where Y is phosphorous.
4. A method in accordance with claim 1, where Y is arsenic.
5. A method in accordance with claim 1, where Y is antimony.
6. A method in accordance with claim 1, where M is sodium.
7. A method in accordance with claim 1, where R is phenyl.

* * * * *

UNITED STATES PATENT OFFICE
CERTIFICATE OF CORRECTION

PATENT NO. : 3,981,897
DATED : Sept. 21, 1976
INVENTOR(S) : James V. Crivello

It is certified that error appears in the above-identified patent and that said Letters Patent are hereby corrected as shown below:

Column 5, line 24, cancel "Group VA alkali".
Column 5, line 24, cancel "salt" and substitute -compound-.
Column 6, line 4, cancel "compound" and substitute -salt-.

Signed and Sealed this

Fourth Day of January 1977

[SEAL]

Attest:

RUTH C. MASON
Attesting Officer

C. MARSHALL DANN
Commissioner of Patents and Trademarks